(12) United States Patent
Korpela et al.

(10) Patent No.: US 9,823,171 B2
(45) Date of Patent: Nov. 21, 2017

(54) METHOD AND APPARATUS FOR TAKING SLURRY SAMPLES FROM A CONTINUOUS GRAVITY PROCESS FLOW, AND USE OF APPARATUS

(71) Applicant: Outotec (Finland) Oy, Espoo (FI)

(72) Inventors: Tapio Korpela, Helsinki (FI); Christian Von Alfthan, Espoo (FI)

(73) Assignee: Outotec (Finland) Oy, Espoo (FI)

( * ) Notice: Subject to any disclaimer, the term of this patent is extended or adjusted under 35 U.S.C. 154(b) by 385 days.

(21) Appl. No.: 14/427,091

(22) PCT Filed: Sep. 16, 2013

(86) PCT No.: PCT/FI2013/050894
§ 371 (c)(1),
(2) Date: Mar. 10, 2015

(87) PCT Pub. No.: WO2014/041252
PCT Pub. Date: Mar. 20, 2014

(65) Prior Publication Data
US 2015/0241321 A1    Aug. 27, 2015

(30) Foreign Application Priority Data

Sep. 17, 2012 (FI) ..................... 20125956

(51) Int. Cl.
*G01N 1/20* (2006.01)
*G01N 1/10* (2006.01)

(52) U.S. Cl.
CPC ............. *G01N 1/2035* (2013.01); *G01N 1/20* (2013.01); *G01N 2001/1093* (2013.01); *G01N 2001/2092* (2013.01)

(58) Field of Classification Search
CPC ....................................................... G01N 1/20
See application file for complete search history.

(56) References Cited

U.S. PATENT DOCUMENTS 3,149,493 A    9/1964 Mortenson et al.
3,727,739 A *  4/1973 Huntington ............. G01N 1/20
                                                  193/31 R (Continued)

FOREIGN PATENT DOCUMENTS

WO          02/35208 A1     5/2002
WO          03/069313 A1    8/2003
WO       2010/064910 A1     6/2010

OTHER PUBLICATIONS

Von Alfthan, Christian and Kongas, Matti, "Sampling for on-stream analysis and composite samples", Recent Advances in Mineral Processing Plant Design, published Oct. 1, 2009, pp. 155-163.

(Continued)

*Primary Examiner* — Robert R Raevis
(74) *Attorney, Agent, or Firm* — Chernoff Vilhauer LLC

(57) ABSTRACT

A method and an apparatus for taking slurry samples from a continuous gravity process flow (PF). The sampling is carried out in two stages by first and second sampling units (1, 2). The primary sample flow (PSF) and the secondary sample flow (SSF) are arranged as pressureless open-channel type flows, so that the flow rate of the secondary sample flow (SSF) to be led for analysis is approximately proportional to an instantaneous flow rate of the process flow (PF). In the apparatus, the first sampling unit (1) and the second sampling unit (2) comprise venting means (23, 24) adjacent the upper ends (25, 26) of their respective first and second side walls (7, 8; 13; 14) to allow equalizing of the atmospheric pressure prevailing inside and outside the first and second sampling units above free liquid levels (27, 28) of the primary and secondary slurry flows (PSF, SSF) along the entire lengths of the sampling units to form pressure—less open-channel type flow paths for the primary and secondary sample flows (PSF, SSF).

12 Claims, 4 Drawing Sheets

(56) References Cited

U.S. PATENT DOCUMENTS

| | | | | |
|---|---|---|---|---|
| 3,783,695 | A * | 1/1974 | Grothe | G01N 1/2035 73/863.56 |
| 4,771,642 | A * | 9/1988 | Parth | G01N 1/20 73/863.21 |
| 7,549,350 | B2 * | 6/2009 | Graze, Jr. | G01N 1/2252 73/23.31 |
| 7,562,556 | B2 * | 7/2009 | Johnston | G01N 1/2258 134/166 C |
| 2005/0056103 | A1 * | 3/2005 | Hirai | G01N 1/2252 73/864.51 |
| 2009/0308182 | A1 * | 12/2009 | Akers | G01N 1/20 73/863.86 |

OTHER PUBLICATIONS

International Search report from corresponding PCT application No. PCT/FI2013/050894, dated Feb. 10, 2014, 4 pgs.

* cited by examiner

METHOD AND APPARATUS FOR TAKING SLURRY SAMPLES FROM A CONTINUOUS GRAVITY PROCESS FLOW, AND USE OF APPARATUS

CROSS-REFERENCE TO RELATED APPLICATIONS

This is a national stage application filed under 35 USC 371 based on International Application No. PCT/FI2013/050894 filed Sep. 16, 2013 and claims priority under 35 USC 119 of Finnish Patent Application No. 20125956 filed Sep. 17, 2012.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable.

STATEMENT REGARDING PRIOR DISCLOSURES BY THE INVENTOR OR A JOINT INVENTOR

Not Applicable.

FIELD OF THE INVENTION

The present invention relates to a method for taking slurry samples from a continuous gravity process flow of a pressureless open-channel type, wherein the sampling is carried out in two stages. The present invention also relates to an apparatus for taking slurry samples from a continuous gravity process flow. Further, a use of the apparatus for taking slurry samples from a continuous gravity process flow.

BACKGROUND OF THE INVENTION

In the article/"Sampling for on-stream analysis and composite samples" by Christian von Alfthan, Matti Kongas; published in the publication "Recent Advances in Mineral Processing Plant Design", SME, Oct. 1, 2009, by Deepak Malhotra, et al ISBN:978-0-87335-316-8, pp. 155-163/, there is disclosed that it is not practical to feed a full mineral processing plant process flow through an analyzer system in most cases. A representative sample is much easier to handle and analyze accurately. A primary sample is taken from a process stream in one or more steps. The flow rate of the primary sample has to be high enough to allow reliable transfer to an analyzer or composite sampler by pumped or gravity flows. Often the primary sample as to be re-sampled as the sample presentation system to the analyzer uses a lower secondary sample flow rate than the primary sample. The present trend to use high capacity big flotation cells has increased the process flows. Thus frequently two-stage or even three-stage sampling is needed to get a suitable sample flow for analysis. The article further discloses a two-stage sampler intended for sampling gravity flows. The disclosed two-stage sampler is generally suitable for sampling of near horizontal non-pressurized pipes or launders with flows higher than 420 $m^3/h$. The sampler comprises a first sampling unit for taking a primary sample flow from the process flow, and a second sampling unit for taking a secondary sample flow from the primary sample flow. A primary sample flow taken from the process flow has a width which is a portion of the width of the process flow. The primary sample is separated from the process flow by the first sampling unit. The separated primary sample flow is spread widthwise to a larger width. A secondary sample flow is separated by the second sampling unit from the spread primary sample flow. Finally the secondary sample flow is conducted to analysis. The sampling units are vertical cutters which extract a narrow slice from the slurry stream. In the prior art sampler the sample is re-shaped by an inclined top wall of the first sampling cutter from an initially narrow vertical cut to a broad strip with a low horizontal cross-section. This makes it possible to use a second sampling cutter to reduce the sample flow to the required size.

In the described prior art two-stage sampler, in use, both the first sampling unit and the second sampling unit are full of slurry and thus act as pressure samplers. A pressure sampler always gives a constant secondary sample flow which does not depend on the flow rate of the process flow. Therefore, the sampler is not able to give a secondary sample flow which would be proportional to the process flow.

Therefore, the problem is that the prior art two-stage sampler is not very useful to be used for composite sampling (periodic sampling). Principally, there are two reasons for slurry sampling. Firstly, the sample is analyzed in the analyzer to measure a certain instantaneous quality characteristic. The known sampler is quite suitable for that. Another reason for slurry sampling is to obtain correct data of an instantaneous volume flow in the instant of time when the instantaneous quality characteristic occurred. Therefore, there is still a need for a sampler which would be able to give a sample flow which is approximately proportional to an instantaneous flow rate of the process flow to enable correct composite sampling.

Another problem with the known two-stage sampler is that it is sensitive to changes in the process flow. If the process flow increases, backflow from the first sampling unit may occur. Also a backflow from the process flow passing through the second sampling unit may undesirably enter the second sampling unit.

OBJECT OF THE INVENTION

The object of the invention is to eliminate the disadvantages mentioned above.

In particular, it is an object of the invention to provide a sampling method and an apparatus which gives a sample flow for analysis which is approximately proportional to an instantaneous flow rate of the process flow to enable correct composite sampling.

Further, it is an object of the invention to provide a sampling method and an apparatus which are not sensitive to process flow changes.

BRIEF SUMMARY OF THE INVENTION

According to an aspect of the invention, the present invention provides a method for taking slurry samples from a continuous gravity process flow of a pressureless open-channel type, the sampling being carried out in two stages, and said process flow having a first width. In the method a primary sample flow having a second width, which is substantially narrower than the first width, is separated by a first sampling unit from the process flow. The separated primary sample flow is spread widthwise to a third width. A secondary sample flow having a fourth width, which is substantially narrower than third width, is separated by a second sampling unit from the primary sample flow at the position of the third width. The secondary sample flow is conducted to analysis. In accordance with the invention, the primary sample flow and the secondary sample flow are arranged as pressureless open-channel type flows, so that the flow rate of the secondary sample flow to be led for analysis is approximately proportional to an instantaneous flow rate of the process flow.

According to another aspect of the invention, the present invention provides an apparatus for taking slurry samples from a continuous process gravity flow of a pressureless open-channel type flowing in an open launder or in a closed flow channel. The apparatus comprises a first sampling unit for taking a primary sample flow from the process flow, and a second sampling unit for taking a secondary sample flow from the primary sample flow. The first sampling unit comprises substantially vertical first side walls defining a first inlet opening and a first outlet opening therebetween. The first side walls diverge in direction towards the first outlet opening. The first inlet opening is substantially narrower than the first width of the process flow, thereby causing the liquid level of the primary sample flow to be lower than that of the process flow. In accordance with the invention, the first sampling unit and the second sampling unit comprise venting means adjacent the upper end of their respective side walls to allow equalizing of the atmospheric pressure prevailing inside and outside the first and second sampling units above the free liquid levels of the primary and secondary slurry flows along the entire lengths of the sampling units to form pressureless open-channel type flow paths for the primary and secondary sample flows.

According to still another aspect of the invention, the present invention provides use of an apparatus for taking slurry samples from a continuous process gravity flow of a pressureless open-channel type flowing in an open launder or in a closed flow channel. The apparatus comprises a first sampling unit for taking a primary sample flow from the process flow, and a second sampling unit for taking a secondary sample flow from the primary sample flow. The first sampling unit comprises substantially vertical first side walls defining a first inlet opening and a first outlet opening therebetween. The first side walls diverge in direction towards the first outlet opening. The first inlet opening is substantially narrower than the first width of the process flow, thereby causing the liquid level of the primary sample flow to be lower than that of the process flow. In accordance with the invention, the first sampling unit and the second sampling unit comprise venting means adjacent the upper end of their respective side walls to allow equalizing of the atmospheric pressure prevailing inside and outside the first and second sampling units above the free liquid levels of the primary and secondary slurry flows along the entire lengths of the sampling units to form pressureless open-channel type flow paths for the primary and secondary sample flows.

According to still another aspect of the invention, the present invention provides an apparatus for taking slurry samples from a continuous process gravity flow of a pressureless open-channel type flowing in an open launder or in a closed flow channel, the apparatus comprising a first sampling unit having a substantially vertical first side wall defining an inlet opening and outlet opening therebetween, the sidewalls diverging in direction, and a second sampling unit having substantially vertical second side walls. In accordance with the invention, the upper edges of the first and second side walls are substantially horizontal. Preferably, the second sampling unit is disposed at least partially within a space defined by the first sidewalls.

In one embodiment of the invention, in the method, the process flow is adjusted to a flow rate which is high enough to create a flow well behind and adjacent the trailing end of the first sampling unit for preventing any backflow of the process flow back into the first and second sampling units.

In one embodiment of the invention, in the method, the first sampling unit and the second sampling unit are vertical gravity cutter samplers.

In one embodiment of the invention, in the method, the second width is adjustable by adjusting the width of a first inlet opening of the first sampling unit.

In one embodiment of the invention, in the method, the fourth width is adjustable by adjusting the width of a second inlet opening of the second sampling unit.

In one embodiment of the invention, the second sampling unit comprises substantially vertical second side walls defining a second inlet opening therebetween. The second inlet opening is narrower than the primary sample flow. The apparatus further comprises a second outlet via which the secondary sample flow can exit from the second sampling unit.

In one embodiment of the invention, the second inlet opening of the second sampling unit is arranged inside the first sampling unit.

In one embodiment of the invention, the first sampling unit comprises two vertical first side walls, each first side wall having a first length in the flow direction, and a vertical first front edge, the vertical first front edges of the first side walls defining a vertical first inlet opening in between, the first inlet opening having a second width which is substantially narrower than the first width, and the distance between the side walls increases in the lengthwise direction of the walls from the second width to a third width which is greater than the second width, said first side walls limiting a first inner space in between to form a flow path for a primary sample flow which can enter the first inner space via the first inlet opening, each first side wall further having a trailing edge defining a first outlet in between, via which first outlet a main part of the primary sample flow, which passes through the second sampling unit, can exit from the first inner space.

In one embodiment of the invention, the upper ends of the first side walls are substantially horizontal along the first length of the first sampling unit. This enables that the liquid level of the process flow may vary in a wide range without the risk that the flow in the sampling units changes to a pressure flow.

In one embodiment of the invention, the second sampling unit comprises two vertical second side walls each having a second length in the flow direction, and a vertical second front edge, the vertical second front edges of the second side walls defining a vertical second inlet opening in between, the second inlet opening having a fourth width, which is substantially narrower than the third width, said second side walls limiting a second inner space in between to form a flow path for a secondary flow sample which can enter the second inner space via the second inlet opening, and the second inner space is further closed by a back wall, and a second outlet is arranged at the bottom of the second inner space via which the secondary sample flow can exit from the second inner space.

In one embodiment of the invention, the apparatus comprises a cleaning device which is arranged to clean the first inlet opening from any trash which may be stuck into the first inlet opening.

In one embodiment of the invention, the cleaning device comprises a liquid jet nozzle for spraying of cleaning fluid.

In one embodiment of the invention, the apparatus comprises means for adjusting the width of the first inlet opening to adjust the second width of the primary sample flow entering the first sampling unit.

In one embodiment of the invention, the apparatus comprises means for adjusting the width of the second inlet opening to adjust the fourth width of the secondary sample flow entering the second sampling unit.

BRIEF DESCRIPTION OF THE SEVERAL VIEWS OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION OF THE INVENTION

In the following disclosure there are phrases like "the width $l_x$ is a portion of another width $l_y$.". It should be noted that this should not be interpreted in a sense that these widths $l_x$, $l_y$ must necessarily be measured at the same point of the structure. Such phrases should be interpreted in a more general sense. The phrase means that the width $l_x$ is substantially narrower than another width $l_y$ with some certain mutual ratio, e.g. 1:5, 1:10 etc. which may vary depending on the embodiment and adjustments required by process conditions.

Figure 1:
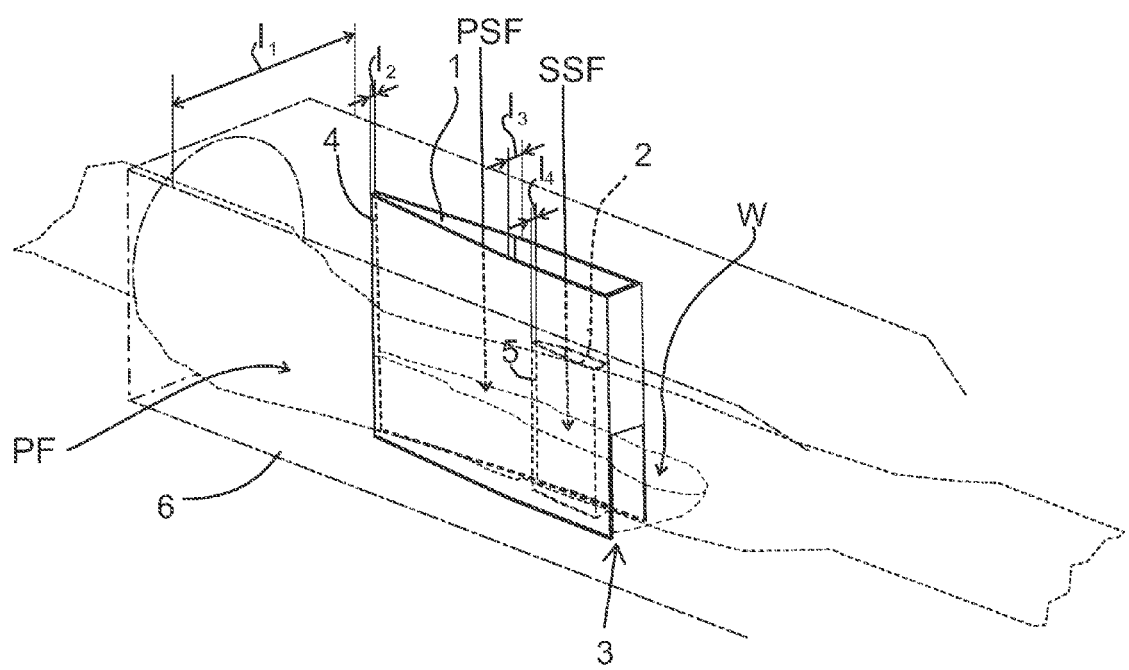
FIG. 1 is an axonometric schematic illustration of an apparatus according to one embodiment of the present invention placed in a flow box, the figure also schematically showing the surface of the process flow flowing through the flow box as a pressureless open-channel type gravity flow.
Figure 2:
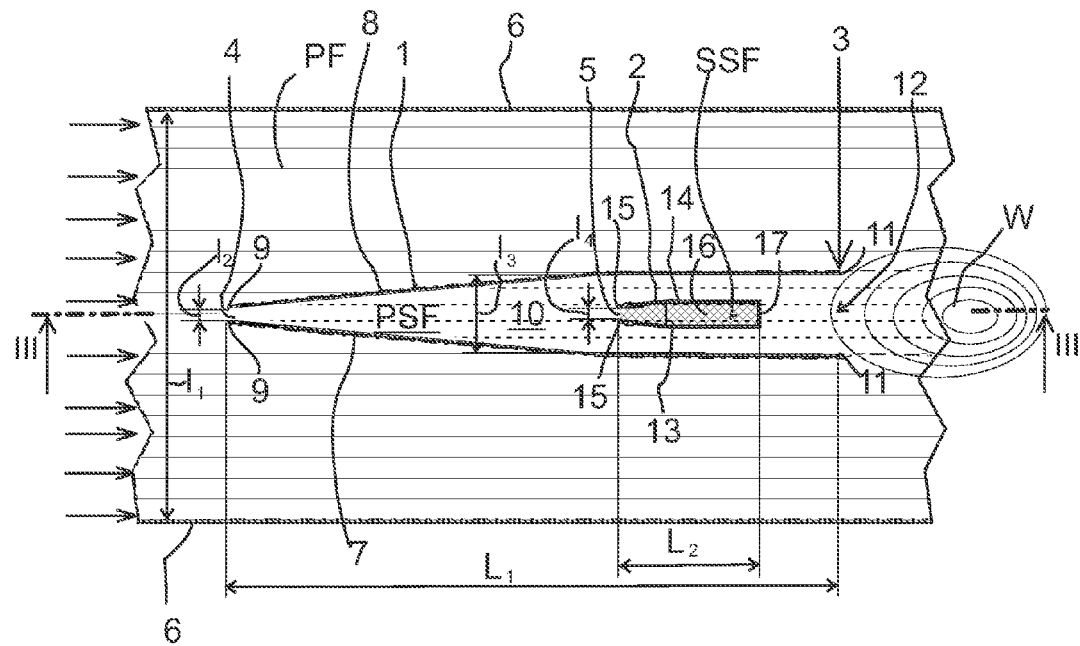
FIG. 2 is a top plan view of the apparatus of FIG. 1.
Figure 3:
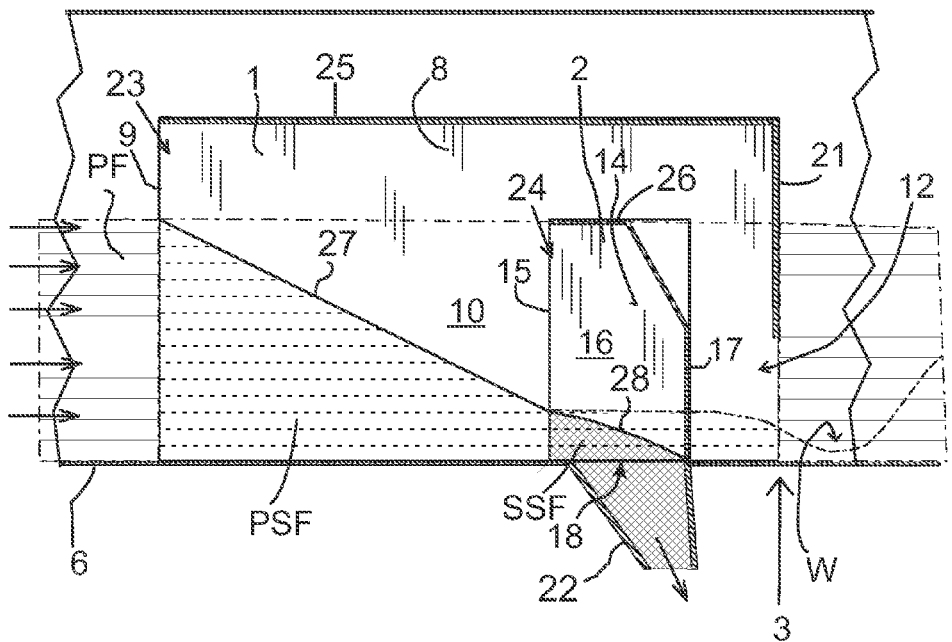
FIG. 3 is a section taken along line III-III from FIG. 2.
Figure 4:
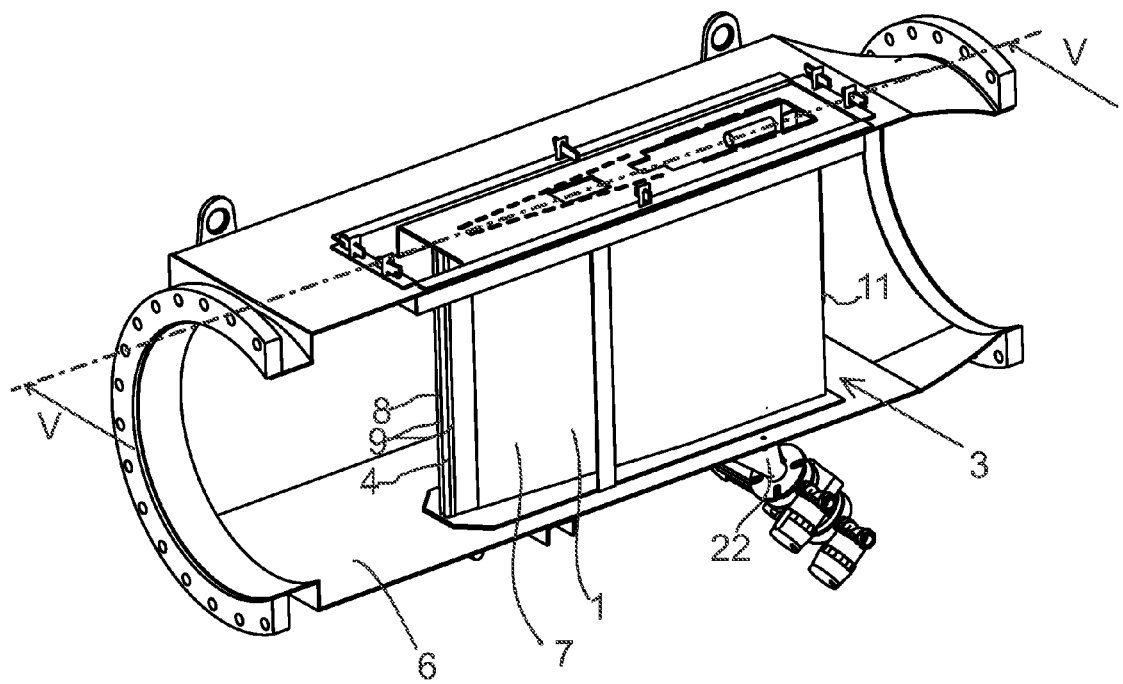
FIG. 4 shows a longitudinal section of a flow channel equipped with one embodiment of an apparatus of the present invention.
Figure 5:
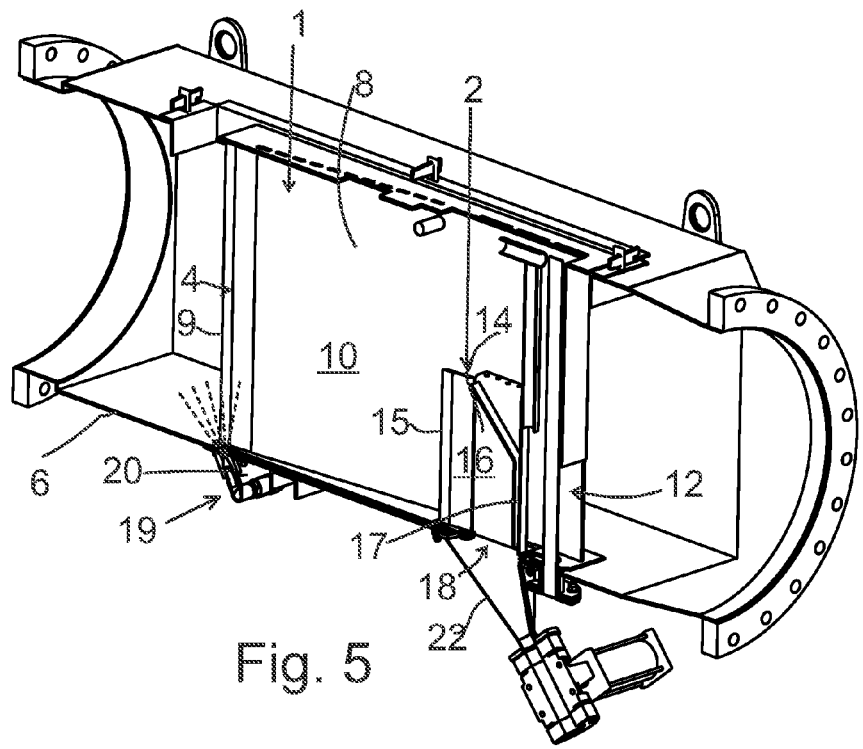
FIG. 5 is a section taken along line V-V from FIG. 4 seen from another direction.

Referring to FIGS. 1 to 3, there is shown an apparatus for taking slurry samples from a continuous process low. The process flow PF is a pressureless open-channel type flow which flows by gravity in an open launder or in a closed flow channel 6, as shown in FIG. 1. The process flow PF flowing in the flow channel 6 has a first width $l_1$. Preferably, as shown in FIGS. 1, 4 and 5, the flow channel 6, wherein sampling the apparatus is placed, is rectangular in cross-section.

The apparatus comprises a first sampling unit 1 for taking a primary sample flow PSF from the process flow PF, and a second sampling unit 2 for taking a secondary sample flow SSF from the primary sample flow PSF.

As shown in FIG. 3, the first sampling unit 1 and the second sampling unit 2 comprise venting means 23, 24 adjacent the upper ends 25, 26 of their respective first and second side walls 7, 8; 13; 14. The venting means allow equalizing of the atmospheric pressure prevailing inside and outside the first and second sampling units above free liquid levels 27, 28 of the primary and secondary slurry flows PSF, SSF. Therefore, they form pressureless open-channel type flow paths for the primary sample flow PSF and the secondary sample flows SSF. This causes that the flow rate of the secondary sample flow SSF to be led for analysis is approximately proportional to an instantaneous flow rate of the process flow PF. Therefore, correct composite sampling results can be achieved. In the embodiment of FIG. 3 the venting means 23 of the first sampling unit 1 is formed by the upper part of the first inlet opening 4 which upper part is above the liquid level of the slurry flow. Likewise, the venting means 23 of the second sampling unit 2 is formed by the upper part of the second inlet opening 5 which upper part is above the liquid level of the slurry flow. In some other embodiments the venting means may be an opening in the structure of the sampling unit at is upper part, or a channel, perforation or any suitable arrangement which allows equalizing of the atmospheric pressure prevailing inside and outside the first and second sampling units above free liquid levels of the primary and secondary slurry flows.

Figure 6:
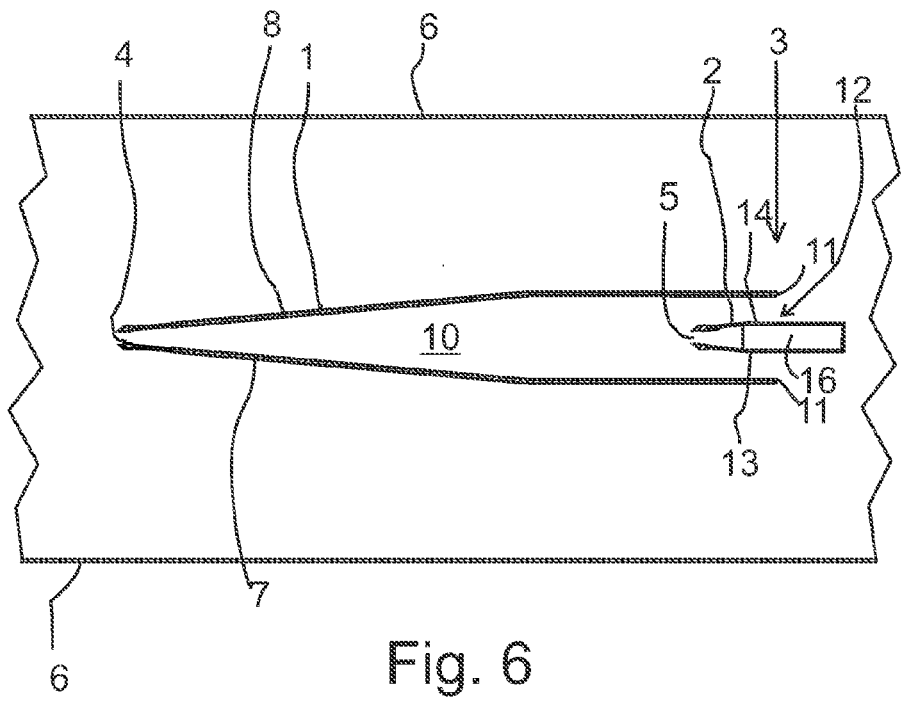
FIG. 6 is a top plan view of the apparatus according to a second embodiment of the present invention.

In the FIGS. 1 to 5, the second sampling unit 2 is arranged inside the first sampling unit 1 at a distance from the trailing end 3 of the first sampling unit 1. However, the second sampling unit 2 does not necessarily have to be located entirely inside the first inner space 10 of the first sampling unit 1. Therefore, as shown in FIG. 6 in another embodiment, it is sufficient for achieving the purposes of the invention that the second inlet opening 5 of the second sampling unit 2 is located between the first side walls 7, 8.

Referring now to FIGS. 2 to 5, the first sampling unit 1 comprises two vertical first side walls 7, 8. The first side walls 7, 8 have a first length $L_1$ in the flow direction, i.e. in the longitudinal direction of the flow channel 6. The first side walls 7, 8 further have a vertical first front edge 9. The vertical first front edges 9 of the first side walls 7, 8 define a vertical first inlet opening 4 in between them. The first inlet opening 4 has a second width $l_2$ which is a portion of the first width $l_1$ dimensioned properly to achieve a suitable flow rate for the primary sample flow PSF. The first inlet opening 4 can cut a narrow slice from the center of the process flow PF.

The upper ends 25 of the first side walls 7, 8 are substantially horizontal along the first length $L_1$ of the first side walls 7, 8.

The distance between the first side walls 7, 8 increases in the lengthwise direction of the walls from the second width $l_2$ to a third width $l_3$ which is greater than the second width $l_2$ so that the primary sample flow PSF spreads to the third width $l_3$. The first side walls 7, 8 limit and define a first inner space 10 in between them. In the shown embodiment, in the diverging portion, the first side walls 7, 8 are straight with a mutual angle of about 12°, but in another embodiment they may be curvedly divergent.

The first inner space 10 between the first side walls forms a flow path for a primary sample flow PSF. The primary sample flow PSF can enter the first inner space 10 via the first inlet opening 4 at the leading end of the first sampling unit 1. The first side walls 7, 8 have a trailing edge 11 defining a first outlet in between them (see FIG. 3). The first sampling unit 1 further comprises a splash shield plate 21 connected to the first side walls 7, 8 above the first outlet 12 to hinder the primary sample flow from splashing out from the first sampling unit 1. The main part of the primary sample flow PSF, which passes through the second sampling unit 2, can exit from the first inner space 10 via the first outlet 12.

In FIG. 2 the second sampling unit 2 is arranged inside the first inner space 10 on the longitudinal symmetry axis of the first sampling unit 1.

Figure 7:
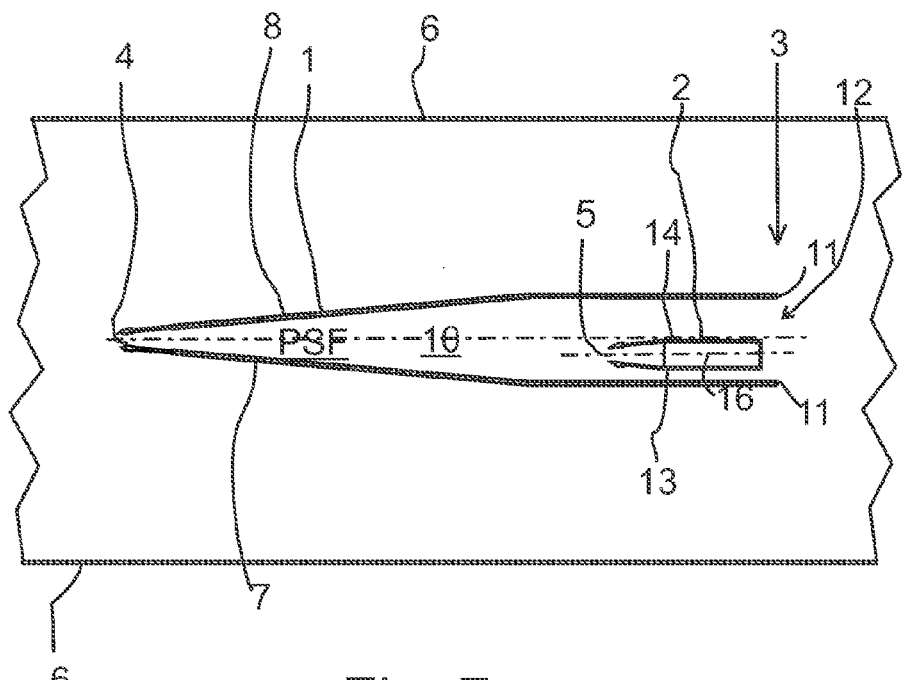
FIG. 7 is a top plan view of the apparatus according to a third embodiment of the present invention.

As shown in the embodiment of FIG. 7 it is also possible to place the second sampling unit 2 so that its symmetry axis is offset from the longitudinal center axis of the first sampling unit 1. Also in some other embodiment it is possible to combine the features of the embodiments of FIGS. 2, 6 and 7.

The second sampling unit 2 comprises two vertical second side walls 13, 14. The second side walls 13, 14 both have a second length $L_2$ in the flow direction, i.e. in the longitudinal direction of the flow channel 6. Further, the second side walls 13, 14 have a vertical second front edge 15. The vertical second front edges 15 of the second side walls 13, 14 define a vertical second inlet opening 5 in between them. The second inlet opening 5 has a fourth width $l_4$, which is a portion of the third width $l_3$ so that a narrow slice can be cut from the center of the primary sample flow PSF.

The second side walls 13, 14 limit and define a second inner space 16 in between them. The second inner space 16 forms a flow path for the secondary flow sample SSF. The secondary flow sample SSF can enter the second inner space 16 via the second inlet opening 5, and the second inner space 16 is further closed by a back wall 17 to lead the stream of secondary flow sample SSF to a second outlet 18. The second outlet 18 is arranged at the bottom of the second inner space 16 so that the secondary sample flow SSF can exit from the second inner space 16 via the second outlet 18. An inclined funnel 22 is arranged at the second outlet 18 to receive the secondary sample flow SSF and to conduct it via a pipeline further to an analyzer (not shown). In the embodiment of FIGS. 4 and 5 the funnel 22 is mounted rotatably at the bottom of the flow channel 6.

As shown in FIG. 5, the apparatus comprises a cleaning device 19 which is arranged to clean the first inlet opening 4 from any trash which may be stuck at the first inlet opening 4. The cleaning device 19 comprises a liquid jet nozzle 20 for spraying of cleaning fluid, e.g. water, to remove the trash.

The apparatus may also comprise means for adjusting the width of the first inlet opening 4 to adjust the second width $l_2$ of the primary sample flow PSF entering the first sampling unit 1. Further, the sampler may also comprise means for adjusting the width of the second inlet opening 5 to adjust the fourth width $l_4$ of the secondary sample flow SSF entering the second sampling unit 2.

The apparatus of FIGS. 1-5 operates in the following way. FIG. 1 shows the outline of the process flow PF flowing through the rectangular flow channel box 6 at the bottom of which the apparatus is placed. Inside the flow channel box 6 the slurry (containing solids and liquid) flows as a continuous gravity process flow PF which is of a pressureless (non-pressurized) open-channel type. The sampling is carried out in two stages by the apparatus. A primary sample flow PSF having a second width $l_2$, which is a portion of the first width $l_1$, is separated by a first sampling unit 1 from the process flow PF. Inside the first sampling unit 1 the separated primary sample flow PSF is spread widthwise to a third width $l_3$. A secondary sample flow SSF having a fourth width $l_4$, which is a portion of the third width $l_3$, is separated by a second sampling unit 2 from the primary sample flow PSF at the position where the primary sample flow has the third width $l_3$. The secondary sample flow SSF is conducted to analysis.

By the arrangement of the venting means 23 and 24 adjacent the upper ends 25 of the first side walls 7, 8 of the first sampling unit 1 and second side walls 13, 14 of the second sampling unit 2 the atmospheric pressure prevailing inside and outside the first and second sampling units is allowed to equalize above the free liquid levels 27, 28 of the primary and secondary slurry flows PSF, SSF to form pressureless open-channel type flow paths for the primary and secondary sample flows PSF, SSF. Therefore, the flow rate of the secondary sample flow SSF to be led for analysis is approximately proportional to an instantaneous flow rate of the process flow PF. The proportionality is further enhanced by that the flow rate of the process flow PF is adjusted high enough to create a flow well W behind and adjacent the trailing end 3 of the first sampling unit 1. The well W is schematically illustrated in FIGS. 1 to 3. The well W is an almost slurry-free air-filled depression in the flow immediately behind the trailing end 3 of the first sampling unit 1. The flow passing through the second sampling unit 2 sweeps up the small backflow from the open well W, so that any backflow of the process flow PF back into the first and second sampling units 1, 2 is prevented and thus only a flow as a secondary sample flow SSF cut from the primary sample flow PSF enters the second sampling unit 2.

It is obvious to a person skilled in the art that with the advancement of technology, the basic idea of the invention may be implemented in various ways. The invention and its embodiments are thus not limited to the examples described above; instead they may vary within the scope of the claims.

The invention claimed is:

1. A method for taking slurry samples from a continuous gravity process flow of a pressureless open-channel type, the sampling being carried out in two stages, and said process flow having a first width, in which method
   a primary sample flow having a second width, which is substantially narrower than the first width, is separated by a first sampling unit from the process flow,
   the separated primary sample flow is spread widthwise to a third width,
   a secondary sample flow having a fourth width, which is substantially narrower than third width, is separated by a second sampling unit from the primary sample flow at the position of the third width, and
   the secondary sample flow is conducted to analysis, characterized in that the primary sample flow and the secondary sample flow are arranged as pressureless open-channel type flows, so that the flow rate of the secondary sample flow to be led for analysis is approximately proportional to an instantaneous flow rate of the process flow; and that the process flow is adjusted to a flow rate which is high enough to create a flow well behind and adjacent the trailing end of the first sampling unit for preventing any backflow of the process flow back into the first and second sampling units.

2. The method according to claim 1, characterized in that the first sampling unit and the second sampling unit are vertical gravity cutter samplers.

3. The method according to claim 1, characterized in that the second width is adjustable by adjusting the width of a first inlet opening of the first sampling unit.

4. The method according to claim 1, characterized in that in the fourth width is adjustable by adjusting the width of a second inlet opening of the second sampling unit.

5. An apparatus for taking slurry samples from a continuous process gravity flow of a pressureless open-channel type flowing in an open launder or in a closed flow channel, said process flow having a first width, the apparatus comprising a first sampling unit for taking a primary sample flow from the process flow, and a second sampling unit for taking a secondary sample flow from the primary sample flow, wherein the first sampling unit comprises substantially vertical first side walls defining a first inlet opening and a first outlet opening therebetween, said first side walls diverging in direction towards the first outlet opening, and in that the first inlet opening is substantially narrower than the first width of the process flow, thereby causing the liquid level of the primary sample flow to be lower than that of the process flow, characterized in that the first sampling unit and the second sampling unit comprise venting means adjacent the upper ends of the side walls to allow equalizing of the atmospheric pressure prevailing inside and outside the first and second sampling units above free liquid levels of the primary and secondary slurry flows along the entire lengths of the sampling units to form pressureless open-channel type flow paths for the primary and secondary sample flows.

6. The apparatus according to claim 5, characterized in that the second sampling unit comprises substantially vertical second side walls defining a second inlet opening therebetween, and that the second inlet opening is narrower than the primary sample flow, and the apparatus comprises a second outlet via which the secondary sample flow can exit from the second sampling unit.

7. The apparatus according to claim 5, characterized in that the second inlet opening of second sampling unit is located inside the first sampling unit.

8. The apparatus according to claim 5, characterized in that the two vertical first side walls of the first sampling unit are further characterized by having a first length in the flow direction, and a vertical first front edge, the vertical first front edges of the first side walls defining a vertical first inlet opening in between, the first inlet opening having a second width which is substantially narrower than the first width, and the distance between the side walls increases in the lengthwise direction of the walls from the second width to a third width which is greater than the second width, said first side walls limiting a first inner space in between to form a flow path for a primary sample flow which can enter the first inner space via the first inlet opening, each first side wall further having a trailing edge defining a first outlet in between, via which first outlet a main part of the primary sample flow, which passes through the second sampling unit, can exit from the first inner space.

9. The apparatus according to claim 8, characterized in that the upper ends of the first side walls are substantially horizontal along the first length.

10. The apparatus according to claim 5, characterized in that the second sampling unit comprises two vertical second side walls each having a second length in the flow direction, and a vertical second front edge, the vertical second front edges of the second side walls defining a vertical second inlet opening in between, the second inlet opening having a fourth width, which substantially narrower than the third width, said second side walls limiting a second inner space in between to form a flow path for a secondary flow sample which can enter the second inner space via the second inlet opening, and the second inner space is further closed by a back wall, and the second outlet is arranged at the bottom of the second inner space via which the secondary sample flow can exit from the second inner space.

11. The apparatus according to claim 5, characterized in that the apparatus comprises a cleaning device which is arranged to clean the first inlet opening from any trash blocking the first inlet opening.

12. The apparatus according to claim 11, characterized in that the cleaning device comprises a liquid jet nozzle for spraying of cleaning fluid.

* * * * *

UNITED STATES PATENT AND TRADEMARK OFFICE
CERTIFICATE OF CORRECTION

| | | |
|---|---|---|
| PATENT NO. | : 9,823,171 B2 | Page 1 of 1 |
| APPLICATION NO. | : 14/427091 | |
| DATED | : November 21, 2017 | |
| INVENTOR(S) | : Tapio Korpela | |

It is certified that error appears in the above-identified patent and that said Letters Patent is hereby corrected as shown below:

In the Specification

Column 6, Line 66   "...defining a first outlet in between them..."
should be -- defining a first outlet 12 in between them --

Signed and Sealed this
Twenty-sixth Day of December, 2017

Joseph Matal
*Performing the Functions and Duties of the
Under Secretary of Commerce for Intellectual Property and
Director of the United States Patent and Trademark Office*